United States Patent [19]

Feeman

[11] Patent Number: 4,851,158

[45] Date of Patent: Jul. 25, 1989

[54] N-ALKYL-N-(AMINOPHENYLSULFONYL)-AMINOALKYLPHOSPHONIC ACIDS

[75] Inventor: James F. Feeman, Wyomissing, Pa.

[73] Assignee: Crompton & Knowles Corporation, Stamford, Conn.

[21] Appl. No.: 123,233

[22] Filed: Nov. 20, 1987

[51] Int. Cl.[4] .................................................. C07F 9/44
[52] U.S. Cl. ...................................... 562/16; 564/15; 562/23
[58] Field of Search ................. 260/397.7 R, 502.5 E, 260/502.5 D; 564/15

[56] References Cited

U.S. PATENT DOCUMENTS 3,910,969  10/1975  Franz .......................... 260/397.7 R
3,911,056  10/1975  Houghton .................... 260/397.7 R

*Primary Examiner*—William R. Dixon, Jr.
*Assistant Examiner*—David M. Brunsman
*Attorney, Agent, or Firm*—Bernard Francis Crowe

[57] ABSTRACT

This invention relates to novel N-alkyl-N-(aminophenylsulfonyl)-aminoalkylphosphonic acids and to processes for their preparation. These compounds are useful as intermediates, especially for the manufacture of dyes containing phosphonic acid groups in their structure. Such dyes are reactive with cellulosic fibers and fabrics in the presence of carbodiimides at elevated temperatures.

11 Claims, No Drawings

N-ALKYL-N-(AMINOPHENYLSULFONYL)-AMINOALKYLPHOSPHONIC ACIDS

This invention relates to novel N-alkyl-N-(aminophenylsulfonyl)-aminoalkylphosphonic acids and to processes for their preparation. These compounds are useful as intermediates, especially for the manufacture of dyes containing phosphonic acid groups in their structure. Such dyes are reactive with cellulosic fibers and fabrics in the presence of carbodiimides at elevated temperatures, and the dyeings produced using them have outstanding light and wet fastness. The new intermediates are readily manufactured at reasonable cost.

The novel organic compounds of this invention have the formula:

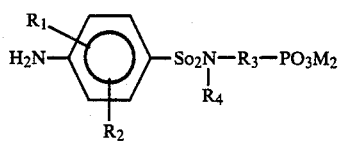

wherein:
$R_1$ is H, lower alkyl, chloro, lower alkoxy, $-CO_2M$;
$R_2$ is H, —lower alkyl, lower alkoxy, or Cl;
$R_3$ is lower alkylene;
$R_4$ is lower alkyl; and
M is H, Na, Li, K, Mg, Ca, $NH_4$ A preferred group of compounds has the formula:

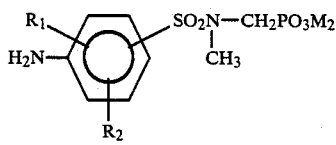

wherein:
$R_1$ is —H, —lower alkoxy, —$CO_2M$;
$R_2$ is —H, —lower alkyl, —lower alkoxy, or —Cl; and
M is —H, —Na, —Li, —K, —Mg, —Ca or $NH_4$.

Especially preferred structures are:

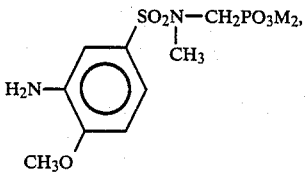

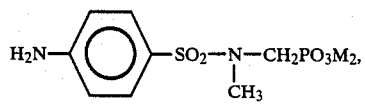

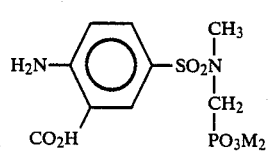

The compounds of this invention can be prepared by chlorosulfonation of a suitably substituted acylanilide having the formula:

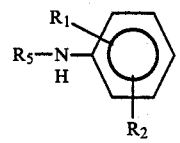

to form the corresponding sulfonyl chloride:

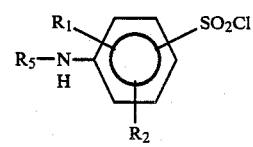

which is subsequently reacted with an alkylaminoalkylphosphonic acid to form the N-alkyl-N-acylaminophenylsulfonyl-aminoalkylphosphonic acid of the formula:

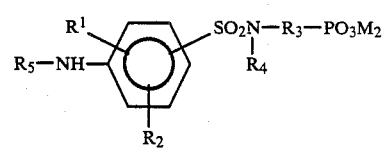

in which $R_5$ is —CO—lower alkyl, —CO—O—lower alkyl or —CO—O—CO— in which one —CO— is bonded to the ring as $R_1$.

Hydrolysis with strong mineral acid or strong base in water removes the acyl group or opens the ring (—CO—O—CO—) to generate the free amine,

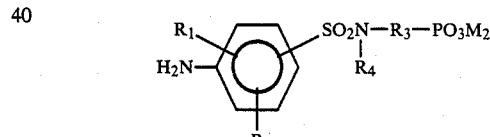

Suitable acylanilide starting materials include, for example: acetyl, formyl or propionyl derivatives of aniline
   o, m or p-toluidine,
     xylidines,
   o, m or p-anisidine,
   2,4- or 2,5-dimethoxyaniline,
     chlorotoluidines,
     p-cresidine,
     dichloroanilines,
     chloroanisidines,
   o, m or p-phenetidine,
     anthranilic acid,
   and isatoic anhydride Certain of the acylanilide sulfonyl chlorides are known compounds.

Suitable alkylaminoalkylphosphonic acids include, for example, those prepared according to the process of my simultaneously filed application, "Process for Preparation of Substituted-Aminomethylphosphonic Acids", i.e.,
   methylaminomethylphosphonic acid ethylaminomethylphosphonic acid
n-propylaminomethylphosphonic acid
isopropylaminomethylphosphonic acid
n-butylaminomethylphosphonic acid
isobutylaminomethylphosphonic acid
sec-butylaminomethylphosphonic acid
n-amylaminomethylphosphonic acid
hexylaminomethylphosphonic acids
heptylaminomethylphosphonic acids
octylaminomethylphosphonic acids
nonylaminomethylphosphonic acids
decylaminomethylphosphonic acids
2-methylaminoethylphosphonic acid.

The compounds of this invention can also be prepared by chlorosulfonation of nitrobenzene or an appropriately substituted nitrobenzene followed by reaction with an alkylaminoalkylphosphonic acid to form the N-alkyl-N-nitrophenylsulfonylaminoalkylphosphonic acid and then by reduction, preferably with hydrogen and a catalyst, to the desired amine.

Suitable nitrobenzene derivatives include, for example, 2,3 or 4-chloronitrobenzene
5-chloro-2-nitroanisole
2-chloro-4-nitrotoluene
2-chloro-6-nitrololuene
4-chloro-2-nitrotoluene
4-chloro-3-nitrotoluene
2,3 or 4-nitroanisole
2,3 or 4-nitrophenetole
2-nitrobenzoic acid
2-nitrobenzoyl chloride
1-nitro-2-propylbenzene
2,3 or 4-nitrotoluene
1,3-dimethyl-2-nitrobenzene
1,2-dimethyl-3-nitrobenzene
1,2-dimethyl-4-nitrobenzene
1,3-dimethyl-4-nitrobenzene
1,3-dimethyl-5-nitrobenzene
2-methyl-3-nitroanisole
3-methyl-2-nitroanisole
3-methyl-4-nitroanisole
4-methyl-3-nitroanisole
5-methyl-2-nitroanisole A number of the sulfonyl chlorides of nitrobenzene and its derivatives, listed above, are well-known compounds.

The reaction of a substituted-phenylsulfonyl chloride with alkylaminoalkylphosphonic acid can be carried out by stirring the solid sulfonyl chloride suspended in an aqueous alkaline solution of the alkali metal salt, —Na, Li or K, while maintaining the pH at 7 to 11 and the temperature at 0°–90° C. Preferred conditions vary somewhat with the reactants, but are generally at temperatures of 25°–50° C., and pH 9–11.

Hydrolysis of the acyl group is readily effected at temperatures of 90°–100° C. for two to three hours using 5 to 10% hydrochloric acid in water.

Catalytic hydrogenation of the nitro group can be carried out using usual catalysts such as paladium or platinum on activated carbon. Reduction of the nitro group can also be carried out by means of sodium sulfide or sodium hydrosulfite in neutral to alkaline aqueous solution in conventional manner.

The products of this invention are particularly useful as a source of phosphonic acid groups for incorporation by reactions such as diazotization and coupling, or by condensation reactions, into dye structures which have reactivity with cellulosic fibers when applied by processes such as given in U.S. Pat. Nos. 4,134,722 and 4,139,345. Novel dye structures in which the products of this invention are incorporated are disclosed in my simultaneously filed applications: "Disazo Reactive Dyes Containing Phosphonic Acid Groups" and "Disazo Reactive Dyes for Cellulosic Fibers".

The invention is illustrated by the following examples in which parts are by weight.

EXAMPLE 1

(a) Preparation of N-(3′-Acetylamino-4′-methoxyphenylsulfonyl)-N-methylaminomethylphosphonic acid To 1400 parts of chlorosulfonic acid was added 331 parts of N-acetyl-2-methoxy-aniline during 1 hour at 30° C. The solution was stirred for 4 hours at 30° C. Pouring in a thin stream into 1000 parts of water and excess ice to maintain the temperature at $-5°$ C.$-0°$ C., with good stirring, gave a white precipitate of the sulfonyl chloride. It was filtered and washed with ice water to remove free acid giving 1021 parts of paste.

The paste was added in 40 minutes to a stirred solution of 200 parts of N-methyl-amino-methylphosphonic acid in 1000 parts of water, 180 parts of 50% sodium hydroxide and ice to 25° C. The pH was kept at 9–10 by addition of more 50% sodium hydroxide solution during the addition of the paste and until it was stable at pH 10. The solution (2900 parts) was clarified through 5 parts of filtercel on a Buchner funnel. Lowering the pH to 5.5 with 239 parts of concentrated hydrochloric acid gave a voluminous crystalline precipitate which was filtered (1001 parts). Analysis by acid hydrolysis and nitrite absorption showed the yield to be 473 parts of N-(3′-acetamino-4′-methoxyphenylsulfonyl)-N-methylaminomethylphosphonic acid (1.344 moles–67.2% of theory). A sample of this intermediate when dried melted at 252°–254° C.

(b) Preparation of N-(3′-Amino-4′-methoxyphenylsulfonyl)-N-methylaminomethylphosphonic Acid A portion of the paste (693 parts) from (a) was added at 60°–90° C. to a mixture of 232.5 parts of water and 270 parts of concentrated hydrochloric acid, heated to 95° C. and held at this temperature for 1 hour. Addition of 700 parts of ice cooled the solution to 20° C. Upon stirring or standing for 24 hours crystals of N-(3′-amino-4′-methoxyphenylsulfonyl)-N-methylaminomethylphosphonic acid formed which melted at 218°–220° C. The hydrolysis solution, after cooling with ice, was used directly for synthesis of dyes; isolation of the product was not necessary.

EXAMPLE 2

Preparation of N-(4′-Aminophenylsulfonyl)-N-methylaminomethylphosphonic Acid and of N-(4′-Acetylaminophenylsulfonyl)-N-methylaminomethylphosphonic Acid N-methylaminomethylphosphonic acid (25 parts) was dissolved in 100 parts of water, and 14 parts of 50% sodium hydroxide solution at pH 7. With stirring 46.7 parts of 4-acetylaminobenzenesulfonylchloride (commercially available; or can be prepared by chlorosulfonation of acetanilide in known manner) was added as a dry solid at 40° C. The pH was then raised to 9 and held there for 1 hour by adding 34 parts of 50% sodium hydroxide solution. The temperature was 40°–48° C. during this time, but then slowly dropped as the pH became stable. During the next hour the remaining small amount of sulfonyl chloride dissolved. Concentrated (31.5%) hydrochloric acid (25 parts) was added to lower the pH to 1 of the solution, which contained N-(4'-acetylaminophenylsulfonyl)N-methylaminomethylphosphonic acid. The solution was heated to 90° C., additional concentrated hydrochloric acid (25 parts) added, and the temperature held at 90°–95° C. for three hours. Product began to crystallize from the hot solution. Cooling to 25° C. and filtering the crystalline precipitate yielded 90.2 parts of paste. Analysis by nitrite absorption indicated 73% yield of isolated material. The melting point of a dried sample of the paste was 237°–239° C. A sample purified by recrystallization from water melted at 241°–243° C.

EXAMPLE 3

Preparation of N-(4-amino-3-carboxyphenylsulfonyl)-N-methylaminomethylphosphonic Acid Isatoic anhydride (163 parts) was added at 12°–27° C. 10 minutes, with cooling, to 476 parts of chlorosulfonic acid. The temperature was raised to 60° in 30 minutes and held at 60°–65° C. for three hours, when hydrogen chloride evolution had stopped. The solution was cooled to 20° C. and added in a thin stream to 500 parts of water and excess ice so that the temperature stayed below 0° C. The gray-white solid precipitate was filtered and washed with ice water until free of sulfuric acid, i.e. filtrate pH above 3, giving 284 parts of paste.

The paste was added at 25°–29° to a solution of 100 parts of N-methylaminomethyl phosphonic acid in 125 parts of water and 64 parts of 50% sodium hydroxide solution. The pH was raised to 9–11 and kept in that range, using 50% sodium hydroxide solution, for two hours. Concentrated hydrochloric acid (481 parts) was added and the temperature held at 95° for three hours to hydrolyze the hetero ring of the original isatoic anhydride to —NH$_2$ and —CO$_2$H. The solution was clarified from a small amount of insoluble impurities and evaporated to 1000 parts volume. The final solution gave no precipitate upon cooling, but absorbed nitrite to produce a diazonium salt which coupled to generate metalizable dyes having outstanding light fastness, indicating that the desired product was present, in solution, although highly water soluble.

What is claimed is:

1. A novel organic compound of the formula:

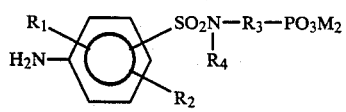

wherein:
R$_1$ is H, lower alkyl, chloro, lower alkoxy, —CO$_2$M;
R$_2$ is H, - lower alkyl, lower alkoxy, or Cl;
R$_3$ is lower alkylene;
R$_4$ is lower alkyl; and
M is H, Na, Li, K, Mg, Ca, NH$_4$.

2. A compound as claimed in claim 1 comprising a preferred group of compounds of the formula:

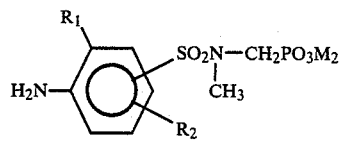

3. A compound as claimed in claim 1 of the formula:

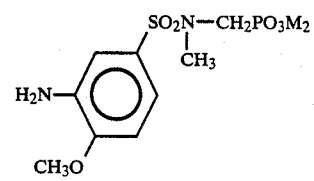

4. A compound as claimed in claim 1 of the formula:

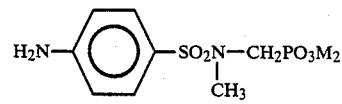

5. A compound as claimed in claim 1 of the formula:

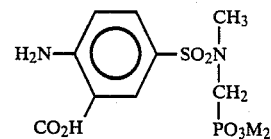

6. A process for the preparation of a compound having the structure:

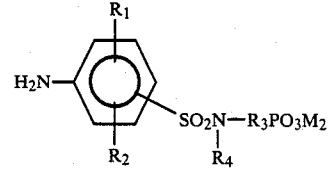

which comprises the steps of:

a. chlorosulfonating a substituted acylanilide having the structure:

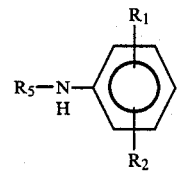

wherein:
R$_1$ is H, lower alkyl, chloro, lower alkoxy, —CO$_2$H, —CO—O—CO— in which one —CO— is bonded to the ring in ortho position to the

group and the other —CO— to the

group:

$R_2$ is —H, lower alkyl, lower alkoxy or Cl;

$R_3$ is lower alkylene $R_4$ is lower alkyl $R_5$ is —CO— lower alkyl, —CO—O—lower alkyl, —CO—O—CO— also bonded to the ring in ortho position to the

group.

b. reacting the resultant acylanilide sulfonyl chloride with an alkylaminoalkyl phosphonic acid in aqueous alkaline medium, and c. hydrolyzing with strong aqueous mineral acid or base.

7. A process according to claim 6 in which: $R_3$ is —$CH_2$—.

8. A process according to claim 6 in which $R_3$ is —$CH_2$—, $R_4$ is —$CH_3$ and $R_5$ is —$COCH_3$, or —CO—O—CO— in which one —CO— is bonded to the phenyl ring in ortho position.

9. A process for the preparation of a compound having the structure:

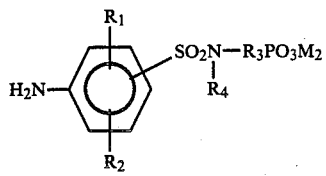

wherein:

$R_1$ is H, —lower alkyl, —lower alkoxy, chloro, —$CO_2H$;

$R_2$ is —H, —lower alkyl, —lower alkoxy, —Cl;

$R_3$ is lower alkylene $R_4$ is lower alkyl which comprises the steps of a. chlorosulfonating a compound having the structure:

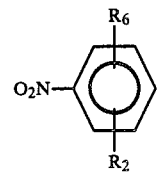

wherein $R_6$ is —H, —Cl, —lower alkyl, —lower alkoxy, —COX in which X is —Cl or —OH;

b. reacting the resultant sulfonyl chloride with an alkylaminoalkylphosphonic acid in aqueous alkaline medium; and c. reducing the nitro group.

10. A process according to claim 9 in which $R_3$ is —$Ch_2$—.

11. A process according to claim 9 in which
$R_1$ is H, $CH_3$, —$OCH_3$, Cl or —$CO_2H$;
$R_2$ is H, —$CH_3$, Cl, —$OCH_3$, —$OC_2H_5$;
$R_3$ is $CH_2$ and
$R_4$ is $CH_3$.

* * * * *